(12) United States Patent
Lubbers et al.

(10) Patent No.: US 7,998,264 B2
(45) Date of Patent: Aug. 16, 2011

(54) HARDENABLE DENTAL MATERIAL

(75) Inventors: Dierk Lubbers, Eichberg (CH); Ralf Kollefrath, Ruthi (CH); Manfred Kalt, Mader (AT)

(73) Assignee: Coltene Whaledent AG, Altstatten (CH)

( * ) Notice: Subject to any disclaimer, the term of this patent is extended or adjusted under 35 U.S.C. 154(b) by 937 days.

(21) Appl. No.: 11/416,379

(22) Filed: May 2, 2006

(65) Prior Publication Data

US 2007/0154861 A1    Jul. 5, 2007

(30) Foreign Application Priority Data

Jan. 5, 2006   (EP) .................................... 06100102

(51) Int. Cl.
*A61C 9/00*   (2006.01)
(52) U.S. Cl. ........................... 106/35; 523/118; 433/214
(58) Field of Classification Search .................... 433/48, 433/214; 523/115, 116, 109, 113, 114, 117, 523/118; 524/439–441; 264/16, 17, 19; 106/35

See application file for complete search history.

(56) References Cited

U.S. PATENT DOCUMENTS

| | | | |
|---|---|---|---|
| 2,941,890 A | | 6/1960 | Zandberg et al. |
| 3,650,031 A | * | 3/1972 | Shilliday ........................ 433/37 |
| 3,921,292 A | * | 11/1975 | Ivchenko ................... 433/199.1 |
| 4,012,838 A | * | 3/1977 | Abdenour ...................... 433/171 |
| 4,713,403 A | | 12/1987 | Yoshida et al. |
| 5,064,891 A | * | 11/1991 | Fujiki et al. ................... 524/264 |
| 5,187,220 A | * | 2/1993 | Richart et al. ................ 524/441 |
| 5,189,077 A | | 2/1993 | Kerby |
| 5,684,060 A | * | 11/1997 | Konings et al. ............... 523/109 |
| 6,116,905 A | * | 9/2000 | Hoos .............................. 433/214 |
| 6,166,123 A | * | 12/2000 | Blatter et al. .................. 524/441 |
| 2002/0119255 A1 | * | 8/2002 | Divigalpitiya et al. ........ 427/421 |
| 2003/0162150 A1 | * | 8/2003 | Engelbrecht et al. .......... 433/223 |
| 2007/0259598 A1 | * | 11/2007 | Ribi .............................. 446/385 |

FOREIGN PATENT DOCUMENTS

| | | |
|---|---|---|
| DE | 3638532 | 5/1988 |
| GB | 1033903 | 2/1963 |
| GB | 2199839 | 7/1988 |
| WO | 9729732 | 8/1997 |

* cited by examiner

*Primary Examiner* — Cris L Rodriguez
*Assistant Examiner* — Eric Rosen
(74) *Attorney, Agent, or Firm* — Katten Muchin Rosenman LLP

(57) ABSTRACT

A hardenable dental material, exhibiting a reflectivity in the hardened state of preferably more than about 70%, measured according to EN ISO 2813 (1999) with an angle of incidence of 60°. The material provides for improved visual readability in the hardened state.

14 Claims, No Drawings

HARDENABLE DENTAL MATERIAL

CROSS-REFERENCE TO RELATED APPLICATION

This application claims priority from European Patent Application no. 06100102, filed on Jan. 5, 2006, the contents of which are herein wholly incorporated by reference.

The present invention relates to the technical field of hardenable dental materials, in particular to dental impression materials.

In various dental applications, e.g. in dental restoration, it is necessary to take an impression of the patient's dental situation, in order to provide the dentist with a 3D model. Such a 3D model needs to resemble the dental situation as exactly as possible in order to provide the dentist with a suitable basis e.g. for a satisfying restoration being prepared, such as a crown, a bridge, or the like. A high accuracy is thus necessary in impression taking and building-up of a 3D model from such an impression.

There are various hardenable dental materials known that allow for an exact reproduction of the dental situation even in the μm range, when utilized correctly. However, the visual readability e.g. for readily checking the accuracy of the impression is hampered: The unaided eye is not able to detect deficiencies in the pure or conventionally coloured, hardened material and/or the impression. Albeit most of the hardenable dental materials are coloured with pigments or the like, the unaided eye is not able to identify fine-structures in these materials.

WO 02/11678 discloses shaped bodies in dental applications that can be scanned by optical systems. These shaped bodies comprise metal or metal alloy powders. In order to allow for readability with dental scanners, the material must not be reflective, because areas which reflect the scanner light are not reproduced in the image. Matt surfaces (either due to the material itself or upon an auxiliary matting agent applied subsequently) are thus needed for use with dental scanners, because reflective surfaces will result in bad spots when read with dental scanners.

It was thus an object of the present invention to overcome the drawbacks of the prior art, especially to allow for an improved readability of a hardenable dental material, in particular an impression material.

This object has been solved by a hardenable dental material, a dental mold, and related methods and uses according to the independent claims.

As used herein and unless otherwise more precisely defined, "dental mold" means any 3-dimensional, shaped body resembling a dental situation, either negative or positive. Most preferably, a dental mold is a negative impression of a dental situation.

As used herein and unless otherwise more precisely defined, "hardenable" means any composition that is initially sufficiently flowable to be applied to a template, and subsequently exhibits an increase in viscosity by setting, curing and/or polymerization, thereby allowing for resembling the 3D situation of said template (examples of such hardenable compositions are e.g. alginate, agar-agar, silicone rubber, polysulfide rubber, and polyether rubber, silginate, gypsum, cast resins, cements, etc.). A hardenable composition can be provided as a one-component composition, but is preferably provided as a two-component composition.

A hardenable dental material according to the invention should exhibit a reflectivity in the hardened state of more than 50%, preferably of more than 60% or about 60%, most preferably of more than about 70%, measured according to EN ISO 2813 (1999) with an angle of incidence of 60° and a thickness of the layer in the hardened state of about 120 μm. The said reflectivity can be established by the person of routine skill in the art by any suitable additive to the composition, as long as such an additive is compatible with the general chemical composition, and as long as the said additive is in conformity with toxicological/medical requirements. It has been found that this reflectivity strikingly enhances the visual readability of the material in the hardened state. Moreover, the diffuse metallic shine additionally enhances the visual readability. The requirements for visual readability on the one hand and readability with dental scanners on the other hand turned out to be contrary: Whereas reflective and metallic shining surfaces as set out above allow for an improved readability and appearance in visual inspection, such reflective and metallic shining surfaces result in bad spots when read with dental scanners.

According to a preferred embodiment, the hardenable dental material may comprise or consist of any material that is known in the art of dental impression taking. Thus, the dental material may in particular comprise or consist of compounds selected from the group consisting of alginate, agar-agar, silicone rubber, polysulfide rubber, and polyether rubber, silginate, and mixtures thereof. Most preferably, the hardenable dental material is provided as a two-component composition, as is known in the art. Hardening of the material occurs either via physico-chemical setting of the composition in case of e.g. gypsum, or chemically by curing, polymerization of the composition, e.g. in case of silicones provided as a two-component composition (base paste and catalyst paste). Most preferably, the hardenable dental material is a silicone-based material, preferably an addition-crosslinkable silicone material, e.g. a dental impression material.

According to yet a further preferred embodiment, the dental material comprises metal or metal alloy particles that are suitably chosen and/or mixed in order to allow for the required reflectivity in the hardened state of the dental material. Mors preferably, the metal or metal alloy particles are to be homogeneously distributed in the dental material. The suitable metal(s) or metal alloy(s) itself and/or its physical form of appearance (particle size, particle shape, etc.) can be chosen and/or, if necessary, determined and evaluated by the person of routine skill in the art by routine experiments. Most preferably, the metal or metal alloy is selected from the group consisting of gold [Au], silver [Ar], platinum [Pt], aluminium [Al], titanium [Ti], copper [Cu], tin (Sn), Zinc (Zn), bronzes and brass, and mixtures thereof.

The invention moreover relates to a dental mold, exhibiting a reflectivity of more than 50%, preferably of more than 60% or about 60%, most preferably of more than about 70%, measured according to EN ISO 2813 (1999) with an angle of incidence of 60° and a thickness of the layer in the hardened state of about 120 μm. Most preferably, said mold is prepared by utilization of a hardenable dental material as set out above, in particular a hardenable dental impression material.

Additionally, the invention relates to a method of enhancing the visual readability of a dental mold as set out above, preferably a dental impression, characterized in that a hardenable dental material as set out above is used in the preparation of the mold.

Thus, a process of dental impression taking according to the invention comprises the steps of:
(i) providing a hardenable dental material as set out above;
(ii) applying said dental material at least partially to the region to be reproduced by the impression;
(iii) allowing said dental material to harden;

(iv) removing said dental material, now carrying the impression, from the region to be reproduced by the impression.

Yet an additional aspect of the invention relates to the use of metal or metal alloy particles in a hardenable dental material as set out above, in particular an impression material, for enhancing the visual readability of said dental material in the hardened state.

A process of manufacture of a hardenable dental material, in particular an impression material, comprises the step of adding at least one substance, in particular metal or metal alloy particles, to the material, wherein the said substance is chosen suchlike to allow for a reflectivity of more than about 50%, preferably of more than about 60%, most preferably of more than about 70% of the hardened composition to be obtained, measured according to EN ISO 2813 (1999) with an angle of incidence of 60° and a thickness of the layer in the hardened state of about 120 μm ($10^{-6}$ m).

The invention will now be described in more detail by means of currently preferred embodiments, without however intending to limit the invention to these embodiments.

Dental impression materials (here: addition crosslinking silicone-based, two-component impression materials, intended for 50/50 mixing of both components) have been prepared according to the following basic formulation:

TABLE 1

Basic formulation

| | | Base paste [parts by weight] | Catalyst paste [parts by weight] |
|---|---|---|---|
| Polymer PTS-P 20'000 | Wacker | 56 | 67.17 |
| Belcron B 6000 | Sihelco AG | 25 | 25 |
| Igepal BC 4 | Tenso Chema | 2 | 2 |
| UOP T-Pulver | UOP M.S.S. | 3 | 3 |
| Aerosil R 972 | Degussa | 2 | 2 |
| Silopren U Vernetzer 430 | Bayer | 12 | 0 |
| Inhibitor PTS-I 27 (DVTMDS) | Wacker | 0 | 0.03 |
| Catalyst liquid (0.3% Pt) | Coltène AG | 0 | 0.8 |
| Additive(s): Metal and/or metal alloy | | [specified individually below] | [specified individually below] |

This basic formulation has been supplemented with the amounts given below in weight percent in both the base paste and the catalyst paste with various additives providing the desired reflectivity of the hardened composition (here: metal (s) and/or metal alloy(s) particles). However, it is to be understood that the additive(s) providing the reflectivity may of course also be supplied in only one component of the two-component composition, e.g. in order to allow for an easy visual control of a thorough and homogeneous mixture of both components being obtained before using the mixed composition.

| Examples according to the invention: | | |
|---|---|---|
| A | "Standart ® Aluminiumpulver Resist 501"; Eckart (Altana); $d_{50}$ = 18 μm | 2,50% |
| B | "Standart ® Aluminiumpulver Resist 501"; Eckart (Altana); $d_{50}$ = 18 μm; and | 1,00 % |
| | "Standart ® Bronzepulver Dorolan 10/0 Reichbleichgold"; Eckart (Altana); $d_{50}$ = 12 μm | 5,00% |

| Comparative Example (not according to the invention): | | |
|---|---|---|
| C | MetalBite ®, R-Dental GmbH (recommended by the supplier for "the powderless optical 3D-data registration (...) (CAD/CAM/CIM-impression technology)" | |

Samples of the compositions A, B and C were evenly spread onto a supply and allowed to cure thereon in an approximate thickness of the resulting hardened composition of about 120 μm. Measurements of the reflectivity of the resulting hardened composition was carried out according to EN ISO 2813: 1999 with an angle of incidence of 60°. Results of these measurements are given as refractometer value in percent.

A: 72%
B: 72-73%
C: 24%

Whereas compositions A and B exhibit a reflectivity of >70%, resulting in an improved visual readability of the hardened compositions due to the reflectivity and the metallic shine, the composition C (not according to the invention, optimized for dental scanners) exhibits a reflectivity which is far below 50%, thus resulting in a matt surface leading to suppression of unwanted reflections in dental scanning applications that would otherwise lead to bad spots in the resulting image. In contrast, compositions A and B exhibited intolerable amounts of bad spots in dental scanning, which make these compositions unsuitable for dental scanning applications.

The invention claimed is:

1. A hardenable dental material that is sufficiently flowable and subsequently exhibits an increase in viscosity thereby allowing it to resemble a 3D situation of a template for taking a dental impression, wherein the hardenable dental material comprises metal or metal alloy particles which exhibit a reflectivity in the hardened state of about 50% or greater measured with an angle of incidence of 60°, wherein the metal or metal alloy particles are homogenously distributed in the dental material and wherein the dental material comprises compounds selected from the group consisting of alginate, agar-agar, silicone rubber, polysulfide rubber, polyether rubber, silginate, silicone-based material and mixtures thereof.

2. The hardenable dental material of claim 1, wherein the metal or metal alloy particles exhibit a reflectivity in the hardened state of about 60% or greater measured with an angle of incidence of 60°.

3. The hardenable dental material of claim 2, wherein the metal or metal alloy particles exhibit a reflectivity in the hardened state of about 70% or greater measured with an angle of incidence of 60°.

4. The hardenable dental material of claim 1, wherein the silicone-based material comprises an addition-crosslinkable silicone material.

5. The hardenable dental material of claim 1, wherein said hardenable dental material comprises a dental impression material.

6. The hardenable dental material of claim 1, wherein said metal is selected from the group consisting of gold, silver, platinum, aluminum, titanium, copper, tin, zinc, bronzes and brass.

7. A dental mold comprising the hardenable dental material according to claim 1.

8. The dental mold of claim 7, wherein the dental mold has a reflectivity of about 60% or greater measured with an angle of incidence of 60°.

9. The dental mold of claim 8, wherein the dental mold has a reflectivity of about 70% or greater measured with an angle of incidence of 60°.

10. A process for dental impression taking, comprising the steps of
    (i) providing the dental material according to claim 1;
    (ii) applying said dental material at least partially to a region to be reproduced by the impression;
    (iii) allowing said dental material to harden; and
    (iv) removing said dental material carrying the impression from the region to be reproduced by the impression.

11. A process of manufacture of the hardenable dental material according to claim 1, comprising a step of adding metal or metal alloy particles to a hardenable dental material, wherein said metal or metal alloy particles allow for a reflectivity of more than about 50%, in the hardenable dental material in a hardened state, to be obtained, measured with an angle of incidence of 60°, wherein the metal or metal alloy particles are homogenously distributed in the dental material.

12. The process of manufacture of the hardenable dental material of claim 11, wherein said metal or metal alloy particles allows for a reflectivity of more than about 60%, in the hardened composition, to be obtained, measured with an angle of incidence of 60°.

13. A process of manufacture of the hardenable dental material of claim 11, wherein said metal or metal alloy particles allows for a reflectivity of more than about 70%, in the hardened composition, to be obtained, measured with an angle of incidence of 60°.

14. The process of claim 11, wherein said hardenable dental material is an impression material.

* * * * *